US00PP21261P2

(12) United States Plant Patent
Faraone Mennella

(10) Patent No.: US PP21,261 P2
(45) Date of Patent: Aug. 31, 2010

(54) ***PETUNIA* PLANT NAMED 'A-32'**

(50) Latin Name: *Petunia hybrida*
Varietal Denomination: A-32

(76) Inventor: Renato Faraone Mennella, Azienda Agricola "Farao" di Renato Faraone Mennella Via Ponte di Striano, Sarno (IT) 84087

( * ) Notice: Subject to any disclaimer, the term of this patent is extended or adjusted under 35 U.S.C. 154(b) by 0 days.

(21) Appl. No.: 12/384,612

(22) Filed: Apr. 7, 2009

(51) Int. Cl.
*A01H 5/00* (2006.01)

(52) U.S. Cl. ..... Plt./356

(58) Field of Classification Search ..... Plt./356
See application file for complete search history.

*Primary Examiner*—Annette H Para
(74) *Attorney, Agent, or Firm*—Mark P. Bourgeois

(57) ABSTRACT

A new cultivar of *Petunia* plant named 'A-32' that is characterized by large numbers of pink flowers, good cold temperature tolerance, a prostrate, spreading habit, a short crop time, and the absence of pollen.

1 Drawing Sheet

Botanical classification: *Petunia hybrida.*
Variety denomination: 'A-32'.

BACKGROUND OF THE INVENTION

The present invention relates to a new and distinct cultivar of *Petunia* plant botanically known as *Petunia hybrida* and hereinafter referred to by the cultivar name 'A-32'.

The new *Petunia* is the product of a planned breeding program conducted by the inventor in Sarno, Italy. The objective of the breeding program is to create new *Petunia* cultivars with attractive colors that are male sterile.

'A-32' is a hybrid that originated from a crossing in 2008 of the female or seed parent a proprietary *Petunia* identified as AS203-2 (not patented) and the male or pollen parent a proprietary *Petunia* identified as 2004PK9 (not patented). The resulting seeds were subsequently planted and grown. The cultivar 'A-32' was selected by the inventor in 2008 as a single plant within the progeny of the stated cross in Sarno, Italy.

Asexual reproduction of the new cultivar 'A-32' first occurred by terminal cuttings in 2008 in Sarno, Italy. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Petunia* cultivar 'A-32'. These traits in combination distinguish 'A-32' as a new and distinct cultivar apart from other existing known varieties of *Petunia.*

1. *Petunia* 'A-32' exhibits a large number of pink flowers.
2. *Petunia* 'A-32' exhibits a short crop time even under short day length conditions.
3. *Petunia* 'A-32' exhibits a prostate, spreading habit.
4. *Petunia* 'A-32' exhibits good cold temperature tolerance.
5. *Petunia* 'A-32' is male sterile and produces no pollen.

The closest comparison cultivars are *Petunia* 'Conchita Evening Glow' (not patented) and *Petunia* 'Conchita Morning Haze' (not patented).

'A-32' is distinguishable from 'Conchita Evening Glow' by the following characteristics:

1. 'A-32' has smaller pink flowers. The flowers of 'Conchita Evening Glow' are purple.

2. 'A-32' has smaller green leaves. The leaves of 'Conchita Evening Glow' are yellow green.
3. 'A-32' has a shorter crop time.
4. 'A-32' exhibits better cold temperature tolerance than 'Conchita Evening Glow'.
5. 'A-32' exhibits a larger number of flowers.
6. 'A-32' is male sterile and produces no pollen.

'A-32' is distinguishable from 'Conchita Morning Haze' by the following characteristics:

1. 'A-32' has smaller flowers.
2. 'A-32' has smaller leaves.
3. 'A-32' exhibits a larger number of flowers.
4. 'A-32' is male sterile and produces no pollen.

'A-32' is distinguishable from the female or seed parent AS203-2 by the following characteristics:

1. 'A-32' has pink flowers. The flowers of AS203-2 are darker pink.
2. 'A-32' has smaller flowers.
3. 'A-32' has a larger quantity of flowers.
4. 'A-32' has a larger overall size.
5. 'A-32' exhibits more vigorous growth.

'A-32' is distinguishable from the male or pollen parent 2004PK9 by the following characteristics:

1. 'A-32' is male sterile. 2004PK9 produces fertile pollen.
2. 'A-32' has a larger number of flowers.
3. 'A-32' exhibits more vigorous growth.

BRIEF DESCRIPTION OF THE DRAWING

The accompanying photograph illustrates the distinguishing traits of *Petunia* 'A-32'. The plant in the photograph shows an overall view of 7 month old plants. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Petunia* cultivar named 'A-32'. Data was collected in Sarno, Italy from 7 month old plastic greenhouse grown plants in 12 cm. diameter containers. The time of year was winter and the temperature range was 15-18 degrees Centigrade during the day and 5-8 degrees Centigrade at night. The light level was natural light. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'A-32' has not been tested under all possible conditions and phenotypic differences may be observed with variations in environmental, climatic, and cultural conditions, however, without any variance in genotype.

Botanical classification: *Petunia hybrida* 'A-32'.

Annual or perennial: Annual.

Parentage: 'A-32' is the product of the female or seed parent identified as *Petunia* AS203-2 and the male or pollen parent identified as *Petunia* 2004PK9.

Vigor: Moderate.

Growth habit: Prostrate, bushy.

Plant shape: Prostate, trailing.

Suitable container size: 12 cm. pots.

Height: 5 cm. in height.

Width: 80 cm. in width.

Low temperature tolerance: −6° Centigrade.

High temperature tolerance: 40° Centigrade.

Propagation: Terminal cuttings.

Time to initiate roots in summer: 10 days to initiate roots at 22° Centigrade.

Time to initiate roots in winter: 14 days to initiate roots at 20° Centigrade.

Time to produce a rooted cutting or liner in summer: 20 days at 22° Centigrade.

Time to produce a rooted cutting or liner in winter: 24 days at 20° Centigrade.

Crop time: Approximately 60 days Summer and Winter, day length neutral.

Root system: Fine and fibrous; 20 cm. in diameter; color 1D.

Stem:

- *Basal branching.*—Yes.
- *Average number of lateral branches.*—11.
- *Pinching.*—No.
- *Lateral branch diameter.*—3 mm. in diameter.
- *Lateral branch length.*—15 cm. in length.
- *Internode length.*—15 mm.
- *Stem strength.*—Strong.
- *Stem color.*—146A.
- *Pubescence.*—Covered with fine hairs.

Foliage:

- *Leaf arrangement.*—Alternate before flowering, opposite after flowering.
- *Compound or single.*—Single.
- *Number of leaves per lateral branch.*—25.
- *Leaf shape.*—Ovate.
- *Leaf apex.*—Acute.
- *Leaf base.*—Cuneate.
- *Leaf length.*—4.0 cm. in length.
- *Leaf width.*—3.0 cm. in width.
- *Texture.*—Glabrous both sides.
- *Pubescence.*—Present both sides.
- *Leaf margin.*—Entire.
- *Venation pattern.*—Alternate.
- *Young leaf color* (*upper surface*).—N137B.
- *Young leaf color* (*lower surface*).—138B.
- *Mature leaf color* (*upper surface*).—N137B.
- *Mature leaf color* (*lower surface*).—138B.
- *Vein color* (*upper surface*).—144A.
- *Vein color* (*under surface*).—144A.
- *Leaf attachment.*—Petiolate.
- *Petiole dimensions.*—10 mm. in length, and 2 mm. in diameter.
- *Petiole color.*—144C.
- *Durability of foliage to stress.*—Strong.

Flower:

- *Inflorescence arrangement.*—Alternate, Solitary in leaf axils.
- *Flower type.*—Funnelform, zygomorphic.
- *Quantity of flowers per lateral stem.*—5.
- *Quantity of flower buds per lateral stem.*—20.
- *Quantity of flowers and buds per plant.*—Average 200.
- *Natural flowering season.*—March to November.
- *Time to flower.*—60 days.
- *Rate of flower opening.*—Every 3 to 4 days.
- *Fragrance.*—Slight.
- *Flower bud length.*—3 cm.
- *Flower bud diameter.*—5 mm.
- *Flower bud shape.*—Tubular, pentagonal in cross-section.
- *Bud color.*—70D.
- *Rate of bud opening.*—1 day.
- *Flower aspect.*—Upright.
- *Flower shape.*—Zygomorphic, funnelform, flaring corolla.
- *Flower dimensions.*—4.0 cm. in diameter and 2.5 cm. in height.
- *Flower longevity.*—3 to 5 days.
- *Number of petals.*—5.
- *Fused or unfused.*—Fused.
- *Petal texture.*—Smooth.
- *Petal arrangement.*—Petals fused into round corolla.
- *Petal shape.*—Orbicular.
- *Petal margin.*—Entire.
- *Petal apex.*—Rounded.
- *Petal base.*—Fused.
- *Petal length.*—15 mm.
- *Petal width.*—15 mm.
- *Petal color when opening* (*upper side*).—73A.
- *Petal color when opening* (*under side*).—65B.
- *Petal color fully opened* (*upper side*).—73A.
- *Petal color fully opened* (*under side*).—65B.
- *Self-cleaning or persistent.*—Self-cleaning.

Sepals:

- *Sepal shape.*—Lanceolate.
- *Sepal arrangement.*—Fused at base, flaring, star-shaped.
- *Number of sepals.*—5.
- *Sepal margin.*—Entire.
- *Sepal apex.*—Rounded.
- *Sepal base.*—Fused.
- *Sepal dimensions.*—10 mm. in length and 2 mm. in width.
- *Young sepal color* (*upper side*).—144A.
- *Young sepal color* (*under side*).—144A.
- *Mature sepal color* (*upper side*).—144A.
- *Mature sepal color* (*under side*).—144A.

Calyx:

- *Calyx shape.*—Star-shaped, rotate.
- *Calyx dimensions.*—10 mm. in length and 10 mm. in diameter.

Pedicels:

- *Pedicel length.*—12 mm.
- *Pedicel diameter.*—1.0 mm.
- *Pedicel angle.*—10 degrees from vertical.
- *Pedicel strength.*—Moderate.
- *Pedicel color.*—144A.

Reproduction organs:

*Stamen number.*—5.

*Anther shape.*—Oval, four chambered.

*Anther size.*—2 mm. in length and 1 mm. in width.

*Anther color.*—155C.

*Amount of pollen.*—None, male sterile.

*Pistil number.*—1.

*Pistil length.*—15 mm.

*Stigma shape.*—Round, bifurcate.

*Stigma color.*—144A.

*Style length.*—15 mm.

*Style color.*—155C.

*Ovary color.*—144A.

Fruit and seed: None, sterile.

Disease and pest resistance: Disease and pest resistance has not been observed.

The invention claimed is:

1. A new and distinct variety of *Petunia* plant named 'A-32' as described and illustrated.

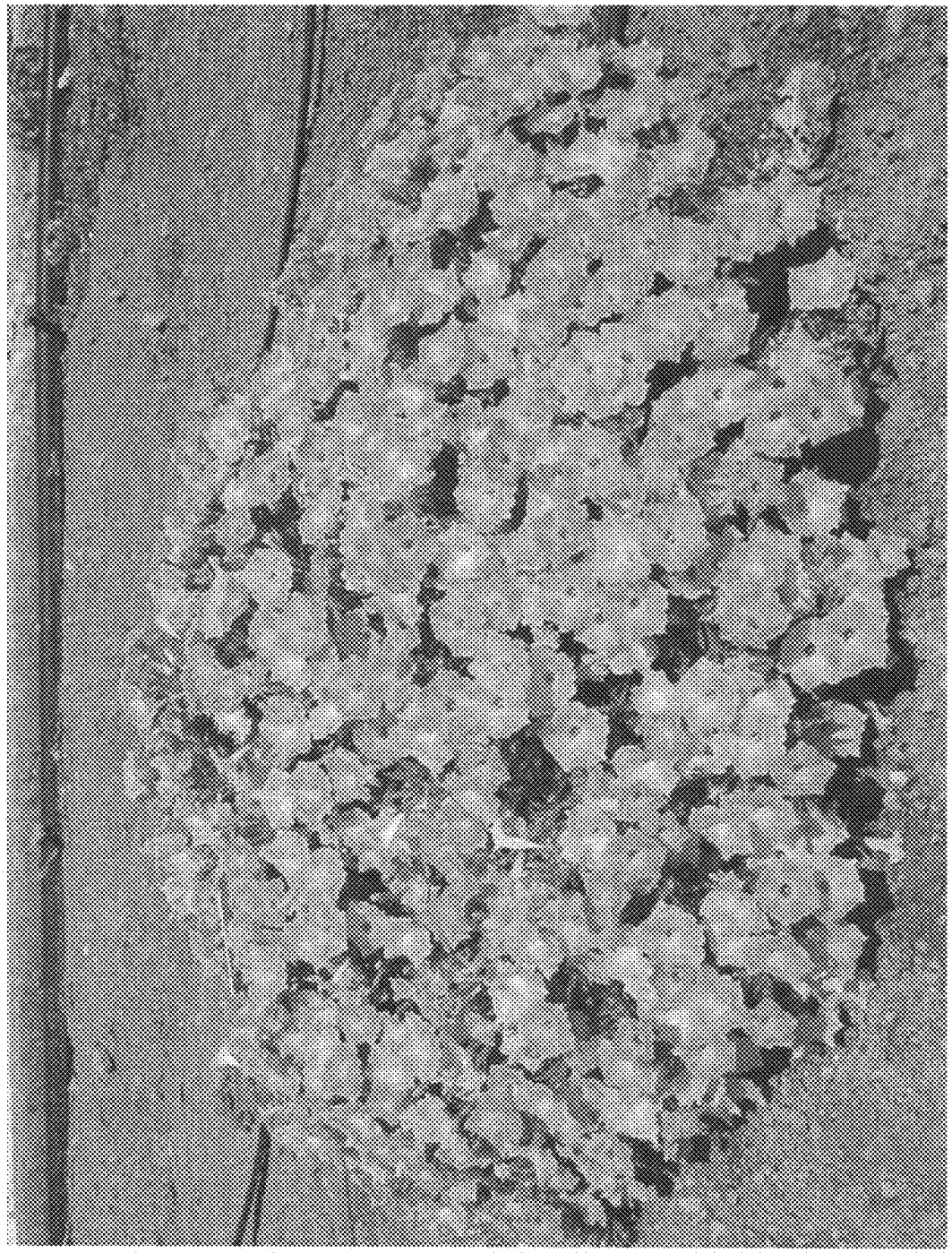

* * * * *